United States Patent
Schoepgens et al.

(10) Patent No.: US 11,077,041 B2
(45) Date of Patent: Aug. 3, 2021

(54) AGENTS FOR REDUCTIVE DECOLOURISATION OF DYED KERATINOUS FIBRES

(71) Applicant: Henkel AG & Co. KGaA, Duesseldorf (DE)

(72) Inventors: Juergen Schoepgens, Schwalmtal (DE); Torsten Lechner, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/688,165

(22) Filed: Nov. 19, 2019

(65) Prior Publication Data
US 2020/0188263 A1    Jun. 18, 2020

(30) Foreign Application Priority Data

Dec. 13, 2018 (DE) .................... 10 2018 221 598.7

(51) Int. Cl.
| | |
|---|---|
| *A61Q 5/08* | (2006.01) |
| *A61K 8/46* | (2006.01) |
| *A61Q 5/10* | (2006.01) |
| *A61K 8/19* | (2006.01) |
| *A61K 8/31* | (2006.01) |
| *A61K 8/41* | (2006.01) |
| *A61K 8/37* | (2006.01) |

(52) U.S. Cl.
CPC ................ *A61K 8/46* (2013.01); *A61K 8/19* (2013.01); *A61K 8/31* (2013.01); *A61K 8/375* (2013.01); *A61K 8/41* (2013.01); *A61Q 5/10* (2013.01); *A61K 2800/4324* (2013.01); *A61K 2800/882* (2013.01)

(58) Field of Classification Search
None
See application file for complete search history.

(56) References Cited

U.S. PATENT DOCUMENTS

| | | |
|---|---|---|
| 2005/0169862 A1 | 8/2005 | De La Mettrie |
| 2017/0112743 A1 | 4/2017 | Schoepgens et al. |
| 2017/0128342 A1* | 5/2017 | Schoepgens ............. A61K 8/86 |
| 2018/0133127 A1* | 5/2018 | Anderheggen .......... A61K 8/22 |
| 2018/0263880 A1 | 9/2018 | Schoepgens et al. |
| 2019/0029934 A1 | 1/2019 | Schoepgens et al. |

FOREIGN PATENT DOCUMENTS

| | | |
|---|---|---|
| DE | 102017204289 A1 | 9/2018 |
| EP | 1300136 A2 | 4/2003 |
| GB | 1501942 A | 2/1978 |
| WO | 2008055756 A2 | 5/2008 |
| WO | 2016005114 A1 | 1/2016 |

* cited by examiner

*Primary Examiner* — Jyothsna A Venkat
(74) *Attorney, Agent, or Firm* — Lorenz & Kopf, LLP

(57) ABSTRACT

The present disclosure relates to multi-component packaging units (kits-of-parts), ready-to-use agents, and methods for reductive decolourisation of dyed keratinous fibres. In one example, the multi-component packaging unit (kit-of-parts) for reductive decolourisation of dyed keratinous fibres includes, (I) a first container (A) including a cosmetic agent (a) and
(II) a second container (B) including a cosmetic agent (b), wherein
the first container (A) and the second container (B) are provided separately from one another,
the cosmetic agent (a) in the first container (A) includes
(a1) one or more reducing agent(s) that is/are solid at room temperature, and
(a2) one or more oxidant(s) that is/are solid at room temperature, and wherein the cosmetic agent (b) in the second container (B) comprises
(b1) one or more alkalising agent(s).

3 Claims, No Drawings ent application EP
AGENTS FOR REDUCTIVE DECOLOURISATION OF DYED KERATINOUS FIBRES

CROSS-REFERENCE TO RELATED APPLICATION

This application claims priority to German Patent Application No. 10 2018 221 598.7, filed Dec. 13, 2018, which is incorporated herein by reference in its entirety.

TECHNICAL FIELD

The present disclosure lies in the field of cosmetics. The present disclosure relates to a multi-component packaging unit (kit-of-parts) for reductive decolourisation of dyed keratin fibres including, separately provided, the two containers (A) and (B). The first container (A) contains a first cosmetic agent (a), which contains one or more reducing agents (a1) which is/are solid at room temperature and one or more oxidants (a2) which is/are solid at room temperature. This/these reducing agent(s) is/are suitable for the reductive decolourisation of artificially dyed hair. This first agent (a) preferably has a low water content or is anhydrous. The container (B) contains a second cosmetic agent (b), which is preferably an aqueous formulation. This second agent (b) is exemplified by its content of one or more alkalising agents (b1).

A further subject of the present disclosure is a ready-to-use agent for the reductive decolourisation of dyed keratinous fibres which is obtained by mixing the two previously described agents (a) and (b).

A third subject of the present disclosure is a method for the reductive decolourisation of dyed keratin fibres, in which the previously described multi-component packaging unit or the ready-to-use decolourising agent is used.

BACKGROUND

Preparations for tinting and colouring hair are an important type of cosmetic agent. They can serve to tint the natural hair colour to a lesser or greater degree depending on the preferences of the person in question, achieve a completely different hair colour, or cover unwanted colour shades, such as shades of grey, for example. Routine hair dyes are formulated either on the basis of oxidation dyes or on the basis of substantive dyes, depending on the desired colour and/or permanency of the dye. Combinations of oxidation dyes and substantive dyes are also frequently used to obtain special nuances.

Dyes formulated on the basis of oxidation dyes lead to brilliant and permanent colour shades. However, they do require the use of strong oxidants, such as hydrogen peroxide solutions, for example. Such dyes contain oxidation dye precursors, or what are known as developer components and coupler components. The developer components either themselves or with coupling with one or more coupler components form, under the influence of oxidants or atmospheric oxygen, the actual colourants per se.

Dyes formulated on the basis of substantive dyes are often used to achieve temporary colours. Substantive dyes are colourant molecules that are taken up directly on the hair and do not require an oxidative process in order to form the colour. Important representatives of this dye class include, for example, triphenylmethane dyes, azo dyes, anthraquinone dyes or nitrobenzene dyes, each of which can carry cationic or anionic groups.

With all said dyeing processes, however, the colour may need to be reversed, either wholly or in part, for various reasons. A partial removal of the colour may be the ideal solution, for example, if the colour result has a darker effect on the fibres than desired. On the other hand, a complete removal of the colour may be desired in some cases. It is conceivable, for example, that the hair is to be coloured or tinted in a particular way for a specific occasion, and the original colour is to be restored after a few days.

Agents and methods for decolourisation are already known from the literature. The oxidative decolourisation of dyed hair, by employing a routine blonding agent for example, is a method long known from the prior art in order to reverse colouring. With this process, however, the fibres can also be damaged through the use of strong oxidants.

Moreover, reductive processes for decolourisation have already been described. European patent application EP 1300136 A2 discloses, for example, a method for hair treatment, wherein the hair is coloured in a first step and then reductively decolourised again in a second step. Said reductive decolourisation is achieved by employing a formulation containing a dithionite salt and a surfactant. In WO 2008/055756 A2, the reductive decolourisation of keratin fibres is achieved using a mixture formed from a reducing agent and an absorption agent.

When reductive decolourising agents are used, the decolourisation effect is achieved by reducing the dyes located on the keratin fibres and/or hair. As a result of the reduction process the dyes are generally converted to their reduced leuco forms. This method involves reducing the double bonds present in the dyes, thus interrupting the chromophoric system of the dyes and converting the dye into a colourless form.

Normally, strong reducing agents must be used for the reduction of dyes. These reducing agents are very reactive compounds that are often unstable in aqueous solution and—depending on the pH value of the solution—quickly decompose to a greater or lesser degree. For example, the reductive decolourising agent sodium dithionite known from the prior art is sensitive to atmospheric oxygen and decomposes slowly in aqueous solution. By increasing the pH value, this decomposition reaction can be delayed. The adjustment to a slightly alkali pH value stabilises aqueous dithionite solutions so that the solution can be stored for several weeks to months with the absence of oxygen. However, if the reductive decolourising agent should be stored for longer or under storage conditions with high temperatures, provision in a solution, particularly a water-containing solution is not the method of choice.

Other reducing agents, such as formamidine sulfinic acid are not stable in aqueous solution, and therefore suitable methods for providing the reducing agent in a storable form are still sought. In WO 2016/005114 A1 the reducing agent is incorporated for example into an anhydrous, fat-containing paste. This paste is then mixed with an aqueous formulation just before use, and the ready-to-use decolourising agent is produced in this way. The reducing agent is then storage-stable for a much longer period of time in an anhydrous environment.

Although the aforementioned provision forms already represent great progress in respect of the stability of the formulation, not all requirements have yet been satisfied in view of the application process. In this regard the inadequate solubility of the reducing agent in the aqueous formulation has proven to be problematic in particular. For example, formamidine sulfinic acid, which is also referred to alternatively as thiourea dioxide, has a particularly poor water solubility of 27 g/l (measured at about 20° C.).

In order to remedy this problem, DE 102017204289 A1 seeks the most convenient ways possible to provide storage-stable decolourising agents. The application describes a multi-component packaging unit which comprises the two agents (a) and (b). The agents (a) and (b) are mixed with one another for use in reductive decolourisation. The agent (a) is preferably provided anhydrously and contains a reducing agent (preferably formamidine sulfinic acid). The agent (b) is preferably aqueous and contains an oxidant. When mixing (a) and (b) the ready-to-use decolourising agent is obtained and heats up—caused by the reaction of reducing agent and oxidant—and in this way ensures rapid dissolution of the reducing agent. Although this possibility for use is quick and convenient, it still has some disadvantages. A significant disadvantage of DE 102017204289 A1 lies in the limited possibility to add an alkalising agent to agent (a) or (b). Reducing agents such as formamidine sulfinic acid develop their greatest decolourising power in an alkaline environment, and the ready-to-use decolourising agent therefore preferably contains at least one alkalising agent in order to set the optimal use conditions. If it is desired to provide the user with a kit comprising just two different preparations, the alkalising agent would therefore have to be incorporated into agent (a) or into agent (b) and thus provided either together with the oxidant or together with the reducing agent. Since both the oxidant and reducing agent can tend towards the development of instabilities in an alkaline environment, in DE 102017204289 A1 particular care must be taken with regard to both the selection of a suitable alkalising agent and the type of provision of agents (a) and (b).

BRIEF SUMMARY

Multi-component packaging units (kits-of-parts), ready-to-use agents, and methods for reductive decolourisation of keratin fibres are provided herein. In an exemplary embodiment, a multi-component packaging unit (kit-of-parts) for reductive decolourisation of dyed keratinous fibres includes,
  (I) a first container (A) including a cosmetic agent (a) and
  (II) a second container (B) including a cosmetic agent (b),
  wherein
    the first container (A) and the second container (B) are provided separately from one another,
    the cosmetic agent (a) in the first container (A) includes
    (a1) one or more reducing agent(s) that is/are solid at room temperature, and
    (a2) one or more oxidant(s) that is/are solid at room temperature, and wherein the cosmetic agent (b) in the second container (B) includes
    (b1) one or more alkalising agent(s).

In an exemplary embodiment, a ready-to-use agent for reductive decolourisation of dyed keratinous fibres includes,
  (a1) one or more reducing agent(s) selected from the group of formamidine sulfinic acid, sodium dithionite, zinc dithionite, potassium dithionite, hydroxymethane sulfinic acid, aminomethane sulfinic acid, cysteine, thiolactic acid, sulfanyl acetic acid (thioglycolic acid), or ascorbic acid, and
  (a2) one or more oxidant(s) selected from the group of sodium percarbonate, potassium percarbonate, sodium perborate, potassium perborate, carbamide peroxide, ammonium persulfate, potassium persulfate, or sodium persulfate, and
  (b1) one or more alkalising agent(s) selected from the group 2-aminoethan-1-ol, 2-amino-2-methylpropan-1-ol, ammonia, arginine, lysine, ornithine, histidine, potassium hydroxide, sodium hydroxide, magnesium hydroxide, calcium hydroxide, sodium metasilicate, potassium metasilicate, potassium hydroxide, sodium hydroxide, sodium carbonate, potassium carbonate, sodium hydrogen carbonate, or potassium hydrogen carbonate.

In an exemplary embodiment, a method for reductive decolourisation of dyed keratinous fibres, includes the following steps in the stated order
  (I) producing a ready-to-use decolourising agent by mixing a cosmetic agent (a) with a cosmetic agent (b), wherein the cosmetic agents (a) and (b) are as defined in claim 1,
  (II) applying the ready-to-use decolourising agent to the dyed keratinous fibres,
  (III) leaving the ready-to-use decolourising agent to take effect, and
  (IV) rinsing out the ready-to-use decolourising agent from the keratinous fibres.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was therefore to provide new provision options, agents and methods which enable convenient, uniform and quick production of a ready-to-use decolourising agent. The ready-to-use decolourising agent produced in this way are intended to decolour the keratin fibres as uniformly and effectively as possible. The decolourising agent should also be exemplified by a high storage stability and also a high decolourising power, even after long storage periods at high temperatures. In order to avoid unnecessarily high amounts of packaging material, the ready-to-use reducing agent should be obtainable in particular by mixing just two preparations.

Surprisingly, it has now been found that the aforementioned object can be achieved outstandingly if the reductive decolourising agent is provided in the form of a special multi-component packaging unit (kit-of-parts). This multi-component packaging unit comprises, separately provided, two containers (A) and (B), wherein the containers (A) and (B) each contain the cosmetic agents (a) and (b). The agent (a) contains at least one reducing agent which is solid at room temperature and additionally at least one oxidant which is solid at room temperature. Agent (a) is particularly preferably provided with a low water content or anhydrously. Agent (b) contains at least one alkalising agent in a preferably water-containing cosmetic carrier.

A first subject of the present disclosure is a multi-component packaging unit (kit-of-parts) for the reductive decolourisation of dyed keratin fibres, comprising, provided separately from one another,
  (I) a first container (A) containing a cosmetic agent (a) and
  (II) a second container (B) containing a cosmetic agent (b),
  wherein
    the agent (a) in the first container (A) contains
    (a1) one or more reducing agents which is/are solid at room temperature, and (a2) one or more oxidants which is/are solid at room temperature, and the agent (b) in container (B) contains (b1) one or more alkalising agents.

The agent (a) contains both one reducing agent which is solid at room temperature and one oxidant which is solid at room temperature. By choosing a solid aggregate state both for the reducing agent and for the oxidant it is possible to provide these two reactive components together in an agent without premature or undesirable reactions occurring.

If reducing agent (a1) and oxidant (a2) are present in solid form in the agent (a), this means that the cosmetic carrier of the agent (a) has been selected such that neither the reducing agent (a1) nor the oxidant (a2) dissolve. In a very particularly preferred embodiment this is achieved in that the agent (a) is provided in a form with a low water content or anhydrously. If the oxidant and reducing agent are present in the agent (a) in solid form, they are also very particularly stable mixed together, since the two solid substances cannot react with one another or can react with one another only to an extremely small extent, and in this way undesirable reactions are avoided or eliminated also over long storage periods.

In order to produce the ready-to-use decolourising agent, the two agents (a) and (b) are now mixed together. During this mixing the reducing agent and the oxidant come into contact with an alkalising agent, the latter preferably being in an aqueous carrier. This contact initiates an exothermic reaction of the components with one another. Due to the exothermy of the reaction and the alkaline medium, the reducing agent and oxidant now dissolve fully, quickly and completely. In this way, the ready-to-use decolourising agent can be produced quickly, conveniently and easily.

The multi-component packaging unit (kit-of-parts) as contemplated herein comprises, separately provided, the two containers (A) and (B) with the agents (a) and (b). A separate provisioning is understood in the sense of the present disclosure to mean that the two agents (a) and (b) are packaged in the containers (A) and (B) such that they do not come into direct contact with one another or cannot be mixed with one another during production of the kit. A mixing of (a) and (b) is possibly only once the containers (A) and (B) have been opened.

Decolourisation of Dyed Keratinous Fibres

Keratinous fibres, keratin-containing fibres or keratin fibres are understood to mean furs, wool, feathers and, in particular, human hair. Although the agents as contemplated herein are primarily suitable for lightening and colouring keratin fibres and/or human hair, they can in principle be used for other purposes also in other fields.

The expression "dyed keratinous fibres" means keratin fibres, which were dyed by employing conventional cosmetic dyes known to a person skilled in the art. The expression "dyed keratinous fibres" means in particular fibres that have been dyed by employing oxidative dyes and/or substantive dyes known from the prior art. In this context, explicit reference is made to the known monographies, for example Kh. Schrader, Grundlagen and Rezepturen der Kosmetika [Cosmetic principles and formulas], $2^{nd}$ Edition, Htithig Buch Verlag, Heidelberg, 1989, which reflect the corresponding knowledge of a person skilled in the art.

Agent (a) in Container (A)

The multi-component packaging unit (kit-of-parts) as contemplated herein comprises a first separately provided container (A) with a cosmetic agent (a). Agent (a) contains, as first ingredient (a1) essential to the present disclosure, at least one reducing agent which is solid at room temperature.

A reducing agent which is solid at room temperature is understood in the sense of the present disclosure to mean that it is solid at a temperature of about 20° C. A solid reducing agent therefore has a melting point above about 20° C. A reducing agent is also understood to mean a substance which is capable of reducing conventional hair dyes, in particular conventional oxidative hair dyes, and thereby converting them into a colourless form, for example their colourless leuco form, Very particularly good results can be obtained by selection of certain reducing agents (a1). Very particularly suitable reducing agents (a1) are selected from the group of formamidine sulfinic acid, sodium dithionite, zinc dithionite, potassium dithionite, hydroxymethane sulfinic acid, aminomethane sulfinic acid, cysteine, thiolactic acid, sulfanyl acetic acid (thioglycolic acid) and/or ascorbic acid, particularly preferably formamidine sulfinic acid.

In a particularly preferred embodiment a multi-component packaging unit (kit-of-parts) as contemplated herein is exemplified in that the agent (a) in the first container (A) contains (a1) one or more reducing agents from the group of formamidine sulfinic acid, sodium dithionite, zinc dithionite, potassium dithionite, hydroxymethane sulfinic acid, aminomethane sulfinic acid, cysteine, thiolactic acid, sulfanyl acetic acid (thioglycolic acid) ascorbic acid and/or salts thereof, particularly preferably formamidine sulfinic acid.

As contemplated herein the reducing agents are from the group of formamidine sulfinic acid, sodium dithionite, zinc dithionite, potassium dithionite, hydroxymethane sulfinic acid, aminomethane sulfinic acid, cysteine, thiolactic acid, sulfanyl acetic acid (thioglycolic acid) ascorbic acid and/or salts thereof which are solid at room temperature, i.e. at a temperature of about 20° C.

Formamidine sulfinic acid is solid at room temperature and has a melting point of about 100° C. Formamidine sulfinic acid is alternatively also referred to as thiourea dioxide or as aminoiminomethane sulfinic acid. Formamidine sulfinic acid has the structure of formula (I), but can also be present in the form of its tautomers. Formamidine sulfinic acid has the CAS number 1758-73-2 and is commercially available from various providers, such as Sigma Aldrich.

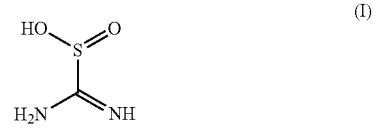

(I)

Sodium dithionite is solid at room temperature and has a melting point of about 80° C., at which it melts with decomposition. Sodium dithionite is an inorganic reducing agent and has the empirical formula $Na_2S_2O_4$ and CAS No. 7775-14-6.

Zinc dithionite is present at about 20° C. in the form of a white powder and is also solid. Zinc dithionite is an inorganic reducing agent and has the empirical formula $ZnS_2O_4$ and CAS No. 7779-86-4.

Potassium dithionite is also solid at room temperature. Potassium dithionite is an inorganic reducing agent and has the empirical formula K2S2O4 and CAS No. 14293-73-3.

Hydroxymethane sulfinic acid is an inorganic reducing agent and has the empirical formula $HO—CH_2—S(O)OH$ and CAS No. 79-25-4. Alternatively, hydroxymethane sulfinic acid is also referred to as formaldehyde sulfoxylic acid. The use of physiologically acceptable salts of hydroxymethane sulfinic acid, for example of the sodium salt and/or the zinc salt, is particularly preferred. Sodium formaldehyde sulfoxylate is solid and has (in the form of the dihydrate) a melting point of about 63° C. Zinc formaldehyde sulfoxylate is also present at about 20° C. in the form of a solid substance. The use of sodium formaldehyde sulfoxylate (sodium hydroxymethanesulfinate, the sodium salt of hydroxymethane sulfinic acid) and/or zinc formaldehyde sulfoxylate (zinc hydroxymethanesulfinate, the zinc salt of hydroxymethane sulfinic acid) is thus likewise possible as contemplated herein.

Aminomethane sulfinic acid is an inorganic reducing agent and has the empirical formula $H_2N—CH_2—S(O)OH$ and CAS No. 118201-33-5. As contemplated herein, both amino methane sulfinic acid itself and the physiologically acceptable salts of amino methane sulfinic acid, for example the sodium salt and/or zinc salt, for example, can be used. The use of sodium amino methane sulfinate (sodium salt of amino methane sulfinic acid) and/or zinc amino methane sulfinate (zinc salt of amino methane sulfinic acid) is therefore likewise possible as contemplated herein.

As contemplated herein cysteine (2-amino-3-sulfanyl propionic acid) means D-cysteine, L-cysteine and/or a mixture of D- and L-cysteine. Cysteine is a colourless solid substance with a melting point of from about 220-228° C.

Thiolactic acid (2-sulfanylpropionic acid) means D-thio lactic acid, L-thio lactic acid and/or a mixture of D- and L-thio lactic acid. The use of thio lactic acid in the form of a physiologically acceptable solid salt is possible as contemplated herein. A preferred salt of thio lactic acid is ammonium thiolactate.

Sulfanyl acetic acid (thioglycolic acid, 2-mercapto-acetic acid) is an organic reducing agent of formula $HS—CH_2—COOH$, and the compound has the CAS No. 68-11-1. In the case of thioglycolic acid, the use of a physiologically acceptable solid salt is possible as contemplated herein. Sodium thioglycolate, potassium thioglycolate and/or ammonium thioglycolate, for example, can be used as physiologically acceptable salts of thiogycolic acid. Ammonium thioglycolate is a preferred physiologically acceptable salt of thioglycolic acid.

As contemplated herein, ascorbic acid means in particular (R)-5-[(S)-1,2-dihydroxyethyl]-3,4-dihydroxy-5H-furan-2-one (further alternative names: vitamin C, L-ascorbic acid) with the CAS No. 50-81-7. Ascorbic acid is solid and has a melting point of from about 190-192° C.

The reducing agent formamidine sulfinic acid has proven to be particularly well suited for use in the kit as contemplated herein. The difficulties associated with the dissolution of formamidine sulfinic acid can be avoided very particularly well by the kit as contemplated herein, and therefore the use of formamidine sulfinic acid is very particularly preferred.

Very particularly preferred therefore is a multi-component packaging unit (kit-of-parts) for the reductive decolourisation of dyed keratin fibres which is exemplified in that the agent (a) in the first container (A) contains
(a1) formamidine sulfinic acid.

Preferred is thus a multi-component packaging unit (kit-of-parts) for the reductive decolourisation of dyed hair comprising, provided separately from one another, (I) a first container (A) containing a cosmetic agent (a) and
(II) a second container (B) containing a cosmetic agent (b),
wherein
the agent (a) in the first container (A) contains
(a1) formamidine sulfinic acid, and
(a2) one or more oxidant(s) which is/are solid at room temperature, and
the agent (b) in container (B) contains
(b1) one or more alkalising agent(s).

The reducing agent(s) from the group (a1) is/are preferably used in the agent (a) within certain amount ranges. The agent (a) preferably contains the reducing agent(s) in a total amount of from about 5.0 to about 80.0% by weight, preferably from about 10.0 to about 70.0% by weight, more preferably from about 20.0 to about 60.0% by weight, and very particularly preferably from about 30.0 to about 50.0% by weight. These amounts in % by weight relate here to the total weight of the agent (a).

Particularly preferred therefore is a multi-component packaging unit (kit-of-parts) for the reductive decolourisation of dyed keratin fibres which is exemplified in that the agent (a) in the first container (A) contains—in relation to the total weight of the agent (a)—one or more solid reducing agent(s) (a1) which are solid at room temperature in a total amount of from about 5.0 to about 80.0% by weight, preferably from about 10.0 to about 70.0% by weight, more preferably from about 20.0 to about 60.0% by weight, and very particularly preferably from about 30.0 to about 50.0% by weight.

The agent (a) as contemplated herein contains, as second constituent (a2) essential to the present disclosure, at least one oxidant which is solid at room temperature. An oxidant which is solid at room temperature is understood in the sense of the present disclosure to mean that it is solid at a temperature of about 20° C. A solid oxidant thus has a melting point above about 20° C.

An oxidant is also understood to mean a substance which is capable of entering into a redox reaction with the aforementioned reducing agents.

Extremely good results can be obtained by selection of certain oxidants (a2) since these can be provided particularly well together with the aforementioned reducing agents, without entering into an undesirable premature reaction or decomposing prematurely during storage. Very particularly suitable solid oxidants (a2) are selected from the group of sodium percarbonate, potassium percarbonate, sodium perborate, potassium perborate, carbamide peroxide, ammonium persulfate, potassium persulfate and sodium persulfate.

Very particularly preferred therefore is a multi-component packaging unit (kit-of-parts) for the reductive decolourisation of dyed keratin fibres which is exemplified in that the agent (a) in the first container (A) contains
(a2) one or more oxidants from the group of sodium percarbonate, potassium percarbonate, sodium perborate, potassium perborate, carbamide peroxide, ammonium persulfate, potassium persulfate and sodium persulfate.

As contemplated herein the oxidants are from the group of sodium percarbonate, potassium percarbonate, sodium perborate, potassium perborate, carbamide peroxide, ammonium persulfate, potassium persulfate and sodium persulfate which are solid at room temperature, i.e. at a temperature of about 20° C.

In the sense of the present disclosure, sodium percarbonate is understood to mean the adduct (or the complex) of sodium carbonate and hydrogen peroxide with the composition 2 $Na_2CO_3 \times 3\ H_2O_2$. Sodium percarbonate forms a white, water-soluble powder, which breaks down upon contact with water into sodium carbonate and hydrogen peroxide. The sodium percarbonate as contemplated herein (2 $Na_2CO_3 \times 3\ H_2O_2$) has a molar mass of 314.02 g/mol and has the CAS number 15630-89-4. Sodium percarbonate melts with decomposition at approximately 60° C. Sodium percarbonate is commercially obtainable in different degrees of purity from various providers. For example, the company Evonik Degussa offers a sodium percarbonate with a purity of about 98.8% by weight.

In the sense of the present disclosure, potassium percarbonate is understood to mean the adduct (or the complex) of potassium carbonate and hydrogen peroxide with the composition 2 $K_2CO_3 \times 3\ H_2O_2$.

Sodium perborate is alternatively also known as sodium peroxoborate. The sodium perborate as contemplated herein is the commercially obtainable sodium peroxoborate tetrahydrate (sodium perborate tetrahydrate) with the empirical formula ($NaBO_3 \cdot 4\ H_2O$). Alternatively, the empirical formula $NaBO_2 \cdot H_2O_2 \cdot 3\ H_2O$ can also be found in the literature. In the solid state, ring-shaped peroxoborates are present, with the formula $Na_2B_2(O_2)_2(OH)_4 \cdot 6\ H_2O$. Sodium perborate tetrahydrate has the CAS No. 10486-00-7 and is sold commercially for example by the company Sigma Aldrich. Sodium perborate is solid at room temperature and melts at approximately 60° C. with decomposition.

Carbamide peroxide is a water-soluble crystalline adduct, which forms during the recrystallisation of urea with concentrated (about 30%) hydrogen peroxide solution and contains approximately 35% hydrogen peroxide. Carbamide peroxide is alternatively also referred to as urea hydrogen peroxide adduct, urea peroxide or urea peroxohydrate and carries the CAS number 124-43-6. Carbamide peroxide is solid at room temperature and melts with decomposition from approximately 75° C.

Ammonium persulfate is alternatively also referred to as ammonium peroxodisulfate and has the empirical formula $(NH_4)_2S_2O_8$. Ammonium persulfate has the CAS number 7727-54-0, is a solid, and melts with decomposition from approximately 120° C.

Potassium persulfate is alternatively also referred to as potassium peroxodisulfate and has the empirical formula $K_2S_2O_8$. Potassium persulfate has the CAS number 7727-21-1, is a solid, and melts with decomposition from approximately 100° C.

Sodium persulfate is alternatively also referred to as sodium peroxodisulfate and has the empirical formula $Na_2S_2O_8$. Sodium persulfate has the CAS number 7775-27-1. Sodium persulfate is a solid substance and melts from approximately 180° C. with decomposition.

The use of sodium percarbonate has proven to be particularly well suited for solving the problem addressed by the present disclosure.

Particularly preferred is thus a multi-component packaging unit (kit-of-parts) for the reductive decolourisation of dyed hair comprising, provided separately from one another,
(I) a first container (A) containing a cosmetic agent (a) and
(II) a second container (B) containing a cosmetic agent (b),
wherein
the agent (a) in the first container (A) contains
(a1) formamidine sulfinic acid, and
(a2) sodium percarbonate, and
the agent (b) in container (B) contains
(b1) one or more alkalising agent(s).

The oxidant(s) (a2) is/are also used in the agent (a) preferably within certain amount ranges. The agent (a) preferably contains one or more oxidants (a2) which is/are solid at room temperature in a total amount from about 0.5 to about 15.0% by weight, preferably from about 1.5 to about 13.5% by weight, more preferably from about 3.5 to about 11.5% by weight, and very particularly preferably from about 5.5 to about 9.5% by weight. These amounts in % by weight relate here to the total weight of the agent (a).

In a further embodiment a very particularly preferred multi-component packaging unit (kit-of-parts) is exemplified in that the agent (a) in the first container (A) contains—in relation to the total weight of the agent (a)—one or more oxidant(s) (a2) which is/are solid at room temperature in a total amount of from about 0.5 to about 15.0% by weight, preferably from about 1.5 to about 13.5% by weight, more preferably from about 3.5 to about 11.5% by weight, and very particularly preferably from about 5.5 to about 9.5% by weight.

It has also proven to be very particularly advantageous if a certain ratio by weight of solid reducing agent (a1) to solid oxidant (a2) is set in the agent (a). The reducing agent(s) is/are very particularly preferably used in the agent (a) in a 50-fold to 2-fold weight excess as compared to the oxidant(s). The reducing agents can in this way react with the oxidant. Here, the oxidant is completely spent and the mixture heats up. Due to the heating of the mixture, the remaining reducing agent dissolves quickly and completely and can thus be used effectively for reductive decolourisation of dyed hair.

The greater is the excess of reducing agent (s), the more substance is available for the reductive decolourisation. On the other hand it is also more difficult to completely dissolve a large amount of reducing agent. For these reasons, the ratio by weight (a1)/(a2) is particularly preferably set to certain ranges lying at values of from about 50.0 to about 2.0, preferably from about 30.0 to about 3.0, particularly preferably from about 10.0 to about 4.0.

In a further embodiment a very particularly preferred multi-component packaging unit (kit-of-parts) is exemplified in that the ratio by weight of the total amount of all reducing agents (a1) contained in the agent (a) to the total amount of all oxidants (a2) contained in the agent (a), i.e. the ratio by weight (a1)/(a2), lies at a value of from about 50.0 to about 2.0, preferably from about 30.0 to about 3.0, particularly preferably from about 10.0 to about 4.0.

The reducing agents (a1) described in the paragraph above are understood to mean the reducing agents which are solid at room temperature (about 20° C.). The oxidants (a2) described in the paragraph above are understood to mean the oxidants which are solid at room temperature (about 20° C.).

The agent (a) is the agent which contains both reducing agents and oxidants. The agent (a) must therefore be satisfy particularly high requirements in respect of the storage stability. The undesirable and premature decomposition of the reducing agents and the undesirable premature reaction of reducing agents and oxidants occur to a greater extent in aqueous solution, and therefore it is particularly preferred if agent (a) is provided substantially anhydrously. The term "substantially anhydrously" is understood here to mean that the water content of the agent (a) is at most about 10.0% by weight. Specific amounts of water can, for example, be introduced to the agent if a raw material in the form of a hydrate or a solution is used. The water content of agent (a), however, is preferably below about 10.0% by weight, more preferably below about 5.0% by weight, even more preferably below about 2.5% by weight, and very particularly preferably below about 0.1% by weight. All specifications in percent by weight are in relation to the total weight of agent (a).

Particularly preferred therefore is a multi-component packaging unit (kit-of-parts) for the reductive decolourisation of dyed keratin fibres which is exemplified in that the agent (a) in the first container (A) has—in relation to the total weight of the agent (a)—a water content below about 10.0% by weight, preferably below about 5.0% by weight, more preferably below about 2.5% by weight, and very particularly preferably below about 0.1% by weight.

The substantially anhydrous agent (a) may be a powder or also a paste, for example. If the agent (a) is used in the form of a powder, dust formation must be avoided and/or the powder must be dedusted. Therefore, it is particularly advantageous if agent (a) is provided in the form of a paste.

In order to obtain a pasty agent (a), for example, the reducing agents (a1) can be incorporated into a fat-containing carrier. In the process, the consistency of the past is co-determined by the melting point or the viscosity of the fatty constituents.

Particularly preferred therefore is a multi-component packaging unit (kit-of-parts) for the reductive decolourisation of dyed keratin fibres which is exemplified in that the agent (a) in the first container (A) contains (a3) one or more fatty constituents from the group of $C_{12}$-$C_{30}$ fatty alcohols $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils.

Agent (a) particularly preferably contains, as ingredients (a3), one or more fatty constituents from the group of $C_{12}$-$C_{30}$ fatty alcohols $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils.

As contemplated herein "fatty constituents" means organic compounds with a water solubility at room temperature (about 22° C.) and atmospheric pressure (about 760 mmHg) of less than about 1% by weight, preferably less than about 0.1% by weight.

The definition of fatty constituents explicitly includes only uncharged (i.e. non-ionic) compounds. Fatty constituents have at least one saturated or unsaturated alkyl group with at least 12 C atoms. The molecular weight of the fatty constituents is at most about 5000 g/mol, preferably at most about 2500 g/mol and particularly preferably at most about 1000 g/mol. The fatty constituents are neither polyalkoxylated nor polyglycerylated compounds. In this regard, polyalkoxylated compounds are compounds for which 2 alkylene oxide units were implemented in the production thereof. Analogously, polyglycerylated compounds are compounds for which two glycerol units were implemented in the production thereof.

Since only non-ionic substances are considered fatty constituents within the context of the present disclosure, charged compounds, such as fatty acids and salts thereof do not fall under the group of fatty constituents.

Preferred fatty constituents are the constituents from the group of $C_{12}$-$C_{30}$ fatty alcohols $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, and hydrocarbons.

The $C_{12}$-$C_{30}$ fatty alcohols can be saturated, mono- or polyunsaturated, linear or branched fatty alcohols with 12 to 30 C atoms.

Examples of preferred linear saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear, unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidonic alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

A $C_{12}$-$C_{30}$ fatty acid triglyceride is understood in the sense of the present disclosure to mean the triester of the trivalent alcohol glycerol with three equivalent fatty acids. Both structurally identical and different fatty acids within a triglyceride molecule can be involved in the ester formations.

Fatty acids, as contemplated herein, are understood to mean saturated or unsaturated, unbranched or branched, unsubstituted or substituted $C_{12}$-$C_{30}$ carboxylic acids. Unsaturated fatty acids can be mono- or polyunsaturated. In the case of an unsaturated fatty acid the C—C double bond(s) thereof can have the cis or trans configuration.

The fatty acid triglycerides are exemplified by particular suitability, wherein at least one of the ester groups starting from glycerol is formed with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachinic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, eleostearic acid [(9Z,11E, 13E)-octadeca-9,11,3-trienoic acid], arachidonic acid [(5Z, 8Z,11Z,14Z)-icosa-5,8,11,14-tetraenic acid] and/or nervonic acid [(15Z)-tetracos-15-enoic acid].

The fatty acid triglycerides can also be of natural origin. The fatty acid triglycerides occurring in soybean oil, peanut oil, olive oil, sunflower oil, macadamia nut oil, moringa oil, apricot kernel oil, marula oil and/or possibly hardened castor oil and mixtures thereof are particularly suitable for use in the agent (a).

A $C_{12}$-$C_{30}$ fatty acid monogylceride is understood to mean the monoester of the trivalent alcohol glycerol with an equivalent fatty acid. Here, either the middle hydroxy group of the glycerol or the terminal hydroxy group of the glycerol can be esterified with the fatty acid.

The $C_{12}$-$C_{30}$ fatty acid monoglycerides that are exemplified by particular suitability are those in which a hydroxy group of the glycerol is esterified with a fatty acid, wherein the fatty acids are selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachinic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenic acid] or nervonic acid [(15Z)-tetracos-15-enoic acid].

A $C_{12}$-$C_{30}$ fatty acid digylceride is understood to mean the diester of the trivalent alcohol glycerol with two equivalent fatty acids. Here, either the middle and a terminal hydroxy group of glycerol can be esterified with two equivalents fatty acid, or both terminal hydroxy groups of glycerol are esterified with one fatty acid each. The glycerol can be esterified here both with two structurally identical fatty acids and with two different fatty acids.

The fatty acid diglycerides that are exemplified by particular suitability are those in which at least one of the ester groups starting from glycerol is formed with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachinic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenic acid] and/or nervonic acid [(15Z)-tetracos-15-enoic acid].

In the context of the present disclosure, a $C_{12}$-$C_{30}$ fatty acid ester is understood to mean the monoester from a fatty acid and an aliphatic monovalent alcohol, wherein the alcohol comprises up to 6 C atoms. Suitable alcohols include, for example, ethanol, n-propanol, isopropanol, 1-butanol, isobutanol, tert-butanol, n-pentanol, iso-pentanol or n-hexanol. Ethanol and isopropanol are preferred alcohols.

Preferred $C_{12}$-$C_{30}$ fatty acid esters are the esters which are formed with esterification of the alcohols ethanol and/or isopropanol with one of the fatty acids from the group dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachinic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenic acid] and/or nervonic acid [(15Z)-tetracos-15-enoic acid]. Isopropyl myristate is very particularly preferred among the fatty acid esters.

Hydrocarbons are exclusively compounds including the atoms hydrocarbon and hydrogen with 8 to 250 C atoms, preferably with 8 to 150 C atoms. In this context, aliphatic hydrocarbons such as mineral oils, liquid paraffin oils (e.g. paraffinum liquidum or paraffinum perliquidum), isoparaffin oils, semi-solid paraffin oils, paraffin waxes, hard paraffin (paraffinum solidum), vaseline and polydecene are preferred in particular.

In this context, liquid paraffin oils (paraffinum liquidum and paraffinum perliquidum) have proven to be particularly suitable. The hydrocarbon is very particularly preferably paraffinum liquidum, also referred to as white oil. Paraffinum liquidum is a mixture of cleaned, saturated, aliphatic hydrocarbons, which are mainly hydrocarbon chains with a C chain distribution of from 25 to 35 C atoms.

The fatty constituents can be the cosmetic carrier of agent (a) and also—depending on the nature and amount of the fat which is used—have a great influence on the consistency of the agent. In this context, it has been found to be particularly preferable if agent (a) has one or more fatty constituents (a3) in a total amount of from about 10 to about 90% by weight, preferably from about 20 to about 60% by weight, and very particularly preferably from about 25 to about 50% by weight, wherein these values are in relation to total weight of the agent (a).

Therefore, particularly preferred is a multi-component packaging unit (kit-of-parts) for reductive decolourisation of dyed keratinous fibres which is exemplified in that agent (a) in the first container (A)—in relation to the total weight of agent (a)—contains one or more fatty constituents (a3) from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils in a total amount of from about 10 to about 90% by weight, preferably from about 20 to about 60% by weight and very particularly preferably from about 25 to about 50% by weight.

The use of hydrocarbons has been found to be very particularly effective for reducing the formation of dust and for inerting the reducing agent with respect to oxygen in the air. In particular, paraffin oils and paraffin waxes have been found to be very compatible with the solid, inorganic reducing agents. For this reason, it is explicitly preferred that one or more hydrocarbons are used as fatty constituents (a3) in a total amount of from about 15.0 to about 90.0% by weight, preferably from about 20.0 to about 85.0 by weight, more preferably from about 25.0 to about 80.0 by weight, and particularly preferably from about 30.0 to about 75.0 by weight—in relation to the total weight of agent (a).

Particularly preferred is also a multi-component packaging unit (kit-of-parts) for the reductive decolourisation of dyed hair, comprising, provided separately from one another, (I) a first container (A) containing a cosmetic agent (a) and (II) a second container (B) containing a cosmetic agent (b), wherein the agent (a) in the first container (A) contains (a1) one or more solid reducing agents from the group of formamidine sulfinic acid, sodium dithionite, zinc dithionite, potassium dithionite, hydroxymethane sulfinic acid, aminomethane sulfinic acid, cysteine, thiolactic acid, sulfanyl acetic acid (thioglycolic acid) ascorbic acid and/or salts thereof, and (a2) one or more solid oxidants from the group of sodium percarbonate, potassium percarbonate, sodium perborate, potassium perborate, carbamide peroxide, ammonium persulfate, potassium persulfate and sodium persulfate, and (a3) one or more fatty constituents (a2) from the group of $C_{12}$-$C_{30}$ fatty alcohols $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, and/or hydrocarbons, and the agent (b) in container (B) contains
(b1) at least one alkalising agent.

Particularly preferred is also a multi-component packaging unit (kit-of-parts) for the reductive decolourisation of dyed hair, comprising, provided separately from one another, (I) a first container (A) containing a cosmetic agent (a) and
(II) a second container (B) containing a cosmetic agent (b),
wherein
the agent (a) in the first container (A) contains
(a1) formamidine sulfinic acid and
(a2) one or more solid oxidants from the group of sodium percarbonate, potassium percarbonate, sodium perborate, potassium perborate, carbamide peroxide, ammonium persulfate, potassium persulfate and sodium persulfate, and
(a3) one or more fatty constituents (a2) from the group of $C_{12}$-$C_{30}$ fatty alcohols $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, and/or hydrocarbons, and
the agent (b) in container (B) contains
(b1) at least one alkalising agent.

Particularly preferred is also a multi-component packaging unit (kit-of-parts) for the reductive decolourisation of dyed hair, comprising, provided separately from one another, (I) a first container (A) containing a cosmetic agent (a) and
(II) a second container (B) containing a cosmetic agent (b),
wherein
the agent (a) in the first container (A) contains
(a1) formamidine sulfinic acid and
(a2) sodium percarbonate and
(a3) one or more fatty constituents (a2) from the group of $C_{12}$-$C_{30}$ fatty alcohols $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, and/or hydrocarbons, and
the agent (b) in container (B) contains
(b1) at least one alkalising agent.

Agent (b) in Container (B)

The second cosmetic agent (b) is situated in the second container (B) of the multi-component packaging unit as contemplated herein. This contains one or more alkalising agents.

Different reducing agents each pass through their optimum effect in a specific pH value range. For example, ready-to-use decolourising agents with formamidine sulfinic acid have their best effect in the alkaline range.

The ready-to-use decolourising agent is—as described above—produced shortly before use by mixing agents (a) and (b) together. The agent (b) is particularly preferably aqueous and contains at least one alkalising agent (b1).

Suitable alkalising agents (b1) can be selected for example from the group of 2-aminoethan-1-ol, 2-amino-2-methylpropan-1-ol, ammonia, arginine, lysine, ornithine, histidine, potassium hydroxide, sodium hydroxide, magnesium hydroxide, calcium hydroxide, sodium metasilicate, potassium metasilicate, potassium hydroxide, sodium hydroxide, sodium carbonate, potassium carbonate, sodium hydrogen carbonate and potassium hydrogen carbonate.

In a further particularly preferred embodiment a multi-component packaging unit (kit-of-parts) as contemplated herein is exemplified in that the agent (b) in the first container (B) contains
(b1) one or more alkalising agents from the group of 2-aminoethan-1-ol, 2-amino-2-methylpropan-1-ol, ammonia, arginine, lysine, ornithine, histidine, potassium hydroxide, sodium hydroxide, magnesium hydroxide, calcium hydroxide, sodium metasilicate, potassium metasilicate, potassium hydroxide, sodium hydroxide, sodium carbonate, potassium carbonate, sodium hydrogen carbonate and potassium hydrogen carbonate.

Since the multi-component packaging unit (kit-of-parts) as contemplated herein makes it possible to provide the alkalising agents (b1) separately from the reducing agents (a1) and the oxidants (a2), the alkalising agents (b1) are not subjected to any limitations in respect of their physical form. In this regard, alkalising agents which are solid at room temperature (about 20° C.) and also alkalising agents which are liquid at room temperature can therefore be selected.

Very particularly suitable alkalising agents have proven to be alkanolamines and ammonia; these are liquid at room temperature. Particularly good decolourisation results could be obtained in particular with 2-aminoethan-1-ol, 2-amino-2-methylpropan-1-ol and ammonia. The alkalising agents from this group increase not only the pH value of an aqueous formulation, but also bring about a swelling of the keratin fibres in addition. In this regard it is alleged that the hair structure of the dyed hair is opened by the swelling, whereby the reducing agents (a1) can diffuse more quickly and better into the hair fibres.

In other words, the multi-component packaging unit as contemplated herein makes it possible to use liquid alkanolamines and ammonia in a decolourisation system based on 2 components. In this way, excellent decolourisation results could be attained alongside a reduction of the packaging costs.

In a very particularly preferred embodiment a multi-component packaging unit (kit-of-parts) as contemplated herein is exemplified in that the agent (b) in the second container (B) contains
(b1) one or more alkalising agents from the group of 2-aminoethan-1-ol, 2-amino-2-methylpropan-1-ol and ammonia.

The amount of alkalising agent (b1) which is used in the agent (b) determines on the one hand the pH value of the mixture and on the other hand also influences the exothermic reaction between reducing agent and oxidant. In this regard the best results could be obtained if one or more alkalising agents (b1) is/are used in the agent (b) in a total amount of from about 0.1 to about 10.0% by weight, preferably from about 0.5 to about 8.0% by weight, more preferably from about 1.0 to about 5.0% by weight, and very particularly preferably from about 1.5 to about 3.5% by weight. All amount specifications for the alkalising agent(s) are in relation to the total weight of agent (b).

In a very particularly preferred embodiment a multi-component packaging unit (kit-of-parts) as contemplated herein is exemplified in that the agent (b) contains—in relation to the total weight of the agent (b)—one or more alkalising agent(s) in a total amount of from about 0.1 to about 10.0% by weight, preferably from about 0.5 to about 8.0% by weight, more preferably from about 1.0 to about 5.0% by weight, and very particularly preferably from about 1.5 to about 3.5% by weight.

In a very particularly preferred embodiment a multi-component packaging unit (kit-of-parts) as contemplated herein is exemplified in that the agent (b) contains—in relation to the total weight of the agent (b)—one or more alkalising agent(s) from the group of 2-aminoethan-1-ol, 2-amino-2-methylpropan-1-ol and ammonia in a total amount of from about 0.1 to about 10.0% by weight, preferably from about 0.5 to about 8.0% by weight, more preferably from about 1.0 to about 5.0% by weight, and very particularly preferably from about 1.5 to about 3.5% by weight.

The agent (b) is preferably provided aqueously or with a water content. The cosmetic agent (b) may be for example an agent with a suitable aqueous or aqueous-alcoholic carrier. Carriers such as creams, emulsions, gels or surfactant-containing foaming solutions, such as shampoos, foaming aerosols, foam formulations or other preparations suitable for application on the hair, can be used for the purpose of reductive decolourisation. The agents for the reductive decolourisation of keratinous fibres are particularly preferably creams, emulsions or free-flowing gels. It is particularly preferred that agent (b) is formulated as an emulsion.

The water content of agent (b)—in relation to the total weight of agent (b)—lies preferably in the range of from about 30 to about 97% by weight, more preferably from about 40 to about 95, even more preferably from about 50 to about 93 and very particularly preferably from about 60 to about 91% by weight.

Very particularly preferred therefore is a multi-component packaging unit (kit-of-parts) for the reductive decolourisation of dyed keratin fibres which is exemplified in that the agent (b) contains—in relation to the total weight of the agent (b)—from about 30 to about 97% by weight, preferably from about 40 to about 95, more preferably from about 50 to about 93 and very particularly preferably from about 60 to about 91% by weight of water.

Particularly preferred is thus also a multi-component packaging unit (kit-of-parts) for the reductive decolourisation of dyed keratinous fibres, comprising, provided separately from one another, (I) a first container (A) containing a substantially anhydrous cosmetic agent (a) and
(II) a second container (B) containing a water-containing cosmetic agent (b),
wherein
the agent (a) in the first container (A) contains
  (a1) one or more reducing agents from the group of formamidine sulfinic acid, sodium dithionite, zinc dithionite, potassium dithionite, hydroxymethane sulfinic acid, aminomethane sulfinic acid, cysteine, thiolactic acid, sulfanyl acetic acid (thioglycolic acid) ascorbic acid and/or salts thereof, particularly preferably formamidine sulfinic acid, and
  (a2) one or more oxidants from the group of sodium percarbonate, potassium percarbonate, sodium perborate, potassium perborate, carbamide peroxide, ammonium persulfate, potassium persulfate and sodium persulfate, and
the agent (b) in container (B) contains
  (b1) one or more alkalising agent(s).

Particularly preferred is thus also a multi-component packaging unit (kit-of-parts) for the reductive decolourisation of dyed keratinous fibres, comprising, provided separately from one another, (I) a first container (A) containing a substantially anhydrous cosmetic agent (a) and
(II) a second container (B) containing a water-containing cosmetic agent (b), wherein
the agent (a) in the first container (A) contains
  (a1) one or more reducing agents from the group of formamidine sulfinic acid, sodium dithionite, zinc dithionite, potassium dithionite, hydroxymethane sulfinic acid, aminomethane sulfinic acid, cysteine, thiolactic acid, sulfanyl acetic acid (thioglycolic acid) ascorbic acid and/or salts thereof, particularly preferably formamidine sulfinic acid, and
  (a2) one or more oxidants from the group of sodium percarbonate, potassium percarbonate, sodium perborate, potassium perborate, carbamide peroxide, ammonium persulfate, potassium persulfate and sodium persulfate, and
the agent (b) in container (B) contains
  (b1) one or more alkalising agent(s),
wherein the ratio by weight of the total amount of all reducing agents (a1) contained in the agent (a) to the total amount of all oxidants (a2) contained in the agent (a), i.e. the ratio by weight (a1)/(a2), lies at a value of from about 50.0 to about 2.0, preferably from about 30.0 to about 3.0, particularly preferably from about 10.0 to about 4.0.

Mixing of Agent (a) Plus (b)

In order to produce the ready-to-use decolourising agent, agents (a) and (b) are mixed with one another, wherein it is provided that the total amount of the agent (a) in container (A) is mixed with the total amount of agent (b) in container (B). In other words the total amount of agent (a) plus (b) represents the ready-to-use decolourising agent.

The mixing can be performed for example in that the total content from container (A) is transferred into container (B) (in this case container (B) is larger than container (A)). It is likewise possible as contemplated herein to transfer the entire content from container (B) into container (A) (in this case container (A) is selected to be larger accordingly).

As agents (a) and (b) are mixed the previously solid reducing agents (a1) and oxidants (a2) from agent (a) are brought into contact with the—preferably aqueous—alkalising agent (b1) from agent (b). With the onset of the dissolution of (a1) and (a2), an exothermic reaction is initiated and is further accelerated by the alkalising agent (b1).

EXAMPLE

Container (A) contains 20 g of agent (a). 8.0 g of formamidine sulfinic acid (a1) are contained in agent (a). The agent (a) contains—in relation to the total weight of agent (a)—40% by weight formamidine sulfinic acid (a) (8.0 g/20 g=40% by weight).

Furthermore, 2.0 g of sodium percarbonate (a2) are contained in agent (a).

The agent (a) contains—in relation to the total weight of agent (a)—10% by weight of sodium percarbonate (a) (2.0 g/20 g=10% by weight).

The ratio by weight of the total amount of all reducing agents (a1) contained in agent (a) to the total amount of all oxidants (a2) contained in agent (a)—in relation to the total weight of agent (a)—is 4.0 (8.0 g/2.0 g=4.0).

In relation to the total amount of agent (a), in the above-mentioned example the reducing agents (a1) are therefore used in a 4-fold excess in comparison to the oxidants (b1). This excess ensures that, once the reducing agents and oxidants have reacted, there is still sufficient reducing agent remaining to reductively decolour the dyed hair. The greater is the excess, the more substance is available for the reductive decolourisation. On the other hand it is also more difficult to completely dissolve a large amount of reducing agent. For these reasons, the ratio by weight (a1)/(b1) is particularly preferably set to certain ranges lying at values of from about 50.0 to about 2.0, preferably from about 30.0 to about 3.0, particularly preferably from about 10.0 to about 4.0.

The containers (A) and (B) of the kit-of-parts as contemplated herein can contain the agents (a) and (b) in different amounts.

In a suitable embodiment the agents (a) and (b) are mixed in a ratio of about 1:1 (for example about 100 g agent (a) and about 100 g agent (b)) (always on the condition that the ratio condition (a1)/(b1) is satisfied).

In order to ensure the most complete dissolution possible of the reducing agent, it is advantageous however if agent (b) is provided in an excess in comparison to agent (a). Thus, it is particularly advantageous if the containers (A) and (B) contain agents (a) and (b) in such amounts that the ratio of agent (a) to agent (b), i.e. the ratio (a)/(b), lies at a value of from about 0.1 to about 1.0, preferably from about 0.15 to about 0.9, more preferably from about 0.18 to about 0.8, and very particularly preferably from about 0.2 to about 0.5.

EXAMPLE

Container (A) contains 10 g of agent (a).
Container (B) contains 100 g of agent (b).
The ratio of agent (a) to agent (b), i.e. the ratio (a)/(b), lies at a value of 10 g/100 g=0.1.

EXAMPLE

Container (A) contains 20 g of agent (a).
Container (B) contains 80 g of agent (b).
The ratio of agent (a) to agent (b), i.e. the ratio (a)/(b), lies at a value of 20 g/80 g=0.25.

Very particularly advantageous is therefore a multi-component packaging unit (kit-of-parts) for reductive decolourisation of dyed keratinous fibres which is exemplified in that the containers (A) and (B) contain agents (a) and (b) in such amounts that the ratio of agent (a) to agent (b), i.e. the ratio (a)/(b), lies at a value of from about 0.1 to about 1.0, preferably from about 0.15 to about 0.9, more preferably from about 0.18 to about 0.8, and very particularly preferably from about 0.2 to about 0.5.

In other words it is very particularly preferred if agents (a) and (b) are contained in the containers (A) and (B) of the multi-component packaging unit as contemplated herein in such amounts that agent (b) is provided in a one-fold to ten-fold excess, very particularly preferably in a two-fold to 5-fold excess, as compared to agent (a).

Agent (a) is preferably free from the above-mentioned alkalising agents. Agent (b) is furthermore preferably free from the above-mentioned reducing agents and oxidants.

2-Component System

The multi-component packaging unit as contemplated herein is a kit which comprises a container (A) and a container (B). In principle, this kit may also comprise further containers, for example a container (C) which contains a conditioner, a shampoo, or an after-treatment agent.

However, it is very particularly preferred if the multi-component packaging unit comprise precisely two containers (A) and (B), i.e. in this case the agents (a) and (b) are provided in the kit, but there are not any further separately provided agents. Should the addition of caring, cleansing or conditioning ingredients be desired within this embodiment, these may be incorporated for example either into agent (a), into agent (b) or also into both agents (a) and (b).

Very particularly preferred therefore is a multi-component packaging unit (kit-of-parts) for the reductive decolourisation of dyed keratinous fibres which comprises precisely two agents (a) and (b) in the two containers (A) and (B).

Further Ingredients in Agents (a) and/or (b)

Agents (a) and/or (b) can additionally also contain further ingredients or active substances. For example, the use of non-ionic surfactants in agents (a) and/or (b) has been found to be particularly advantageous.

The term surfactants is understood to mean amphiphilic (bifunctional) compounds having at least one hydrophobic radical and at least one hydrophilic molecule part. The hydrophobic molecule part is usually a hydrocarbon chain with 10 to 30 carbon atoms. In the case of non-ionic surfactants, the hydrophilic molecule part is an uncharged, highly polar structural unit.

Non-ionic surfactants contain, for example, a polyol group, a polyalkylene glycol ether group or a combination of a polyol and polyglycol ether group as hydrophilic group. Examples of such compounds include addition products of 2 to 50 mol ethylene oxide and/or 2 to 50 mol propylene oxide on linear and branched fatty alcohols with 12 to 30 carbon atoms, fatty alcohol polyglycol ethers or fatty alcohol polypropylene glycol ethers or mixed fatty alcohol polyethers, addition products of 2 to 50 mol ethylene oxide and/or 2 to 50 mol propylene oxide on linear and branched fatty acids with 6 to 30 carbon atoms, fatty acid polyglycol ethers or fatty acid polypropylene glycol ethers or mixed fatty acid polyethers, addition products of 2 to 50 mol ethylene oxide and/or 2 to 50 mol propylene oxide on linear and branched alkyl phenols with 8 to 15 carbon atoms in the alkyl group, alkyl phenol polyglycol ethers or fatty alkyl polypropylene glycol ethers or mixed fatty alkyl phenol polyethers, with a methyl or $C_2$-$C_6$ alkyl radical end-group-closed addition products of 2 to 50 mol ethylene oxide and/or 2 to 5 mol propylene oxide on linear and branched fatty alcohols with 8 to 30 carbon atoms on fatty acids with 8 to 30 C atoms and on alkyl phenols with 8 to 15 C atoms in the alkyl group, such as the types available under the trade names Dehydol® LS, Dehydol® LT (Cognis), $C_{12}$-$C_{30}$ fatty acid mono- and diesters of addition products of 2 to 30 mol ethylene oxide on glycerol, addition products of 5 to 60 mol ethylene oxide on castor oil and hardened castor oil, polyol fatty acid esters, such as the commercially available products Hydagen® HSP (Cognis) or Sovermol® (Cognis), polyalkoxylated triglycerides, polyalkoxylated fatty acid alkyl esters with the formula (Tnio-1)

$$R^1CO\text{---}(OCH_2CHR^2)_wOR^3 \qquad (\text{Tnio-1})$$

wherein $R^1CO$ denotes a linear or branched, saturated and/or unsaturated acyl radical having 6 to 22 carbon atoms, $R^2$ denotes hydrogen or methyl, $R^3$ denotes linear or branched alkyl radicals having 1 to 4 carbon atoms and w denotes numbers from 2 to 20, amine oxides, hydroxy mixed ethers, as described for example in DE-OS 197 38 866, sorbitan fatty acid esters and addition products of ethylene oxide on sorbitan fatty acid esters, such as polysorbates, sugar fatty acid esters and addition products of ethylene oxide on sugar fatty acid esters, addition products of ethylene oxide on fatty acid alkanolamides and fatty amines, sugar-based surfactants of the alkyl and alkenyl oligoglycoside type or sugar-based surfactants of the fatty acid N-alkylpolyhydroxyalkylamide type.

$C_{12}$-$C_{30}$ fatty alcohols, $C_{12}$-$C_{30}$ (fatty acid triglycerides, $C_{12}$-$C_{30}$ fatty acid monoglycerides, $C_{12}$-$C_{30}$ fatty acid diglycerides and $C_{12}$-$C_{30}$ fatty acid esters have a highly polar end group (which can also be seen in the low HLB values of the compounds of this group). In the context of this present disclosure, they are considered fatty components and, therefore, are non-ionic surfactants according to the definition of the present disclosure.

Furthermore, agents (a) and/or (b) can also contain one or more non-ionic polymers.

Polymers are macromolecules having a molecular weight of at least about 1000 g/mol, preferably at least about 2500 g/mol, particularly preferably at least about 5000 g/mol, which include the same, repeating organic units. Polymers are produced by polymerisation of a monomer type or by polymerisation of different, structurally different monomer types. If the polymer is produced by polymerisation of one monomer type, it is referred to as a homopolymer. If structurally different monomer types are used in the polymerisation, they are referred to as copolymers by a person skilled in the art.

The maximum molecular weight of the polymer depends on the degree of polymerisation (number of polymerised monomers) and is partly determined by the polymerisation method. In the sense of the present disclosure, the maximum molecular weight of the zwitterionic polymer (d) is preferably no more than about $10^7$ g/mol, more preferably no more than about $10^6$ g/mol, and particularly preferably no more than about $10^5$ g/mol.

Non-ionic polymers do not have any charges.

Examples of suitable non-ionic polymers are vinyl pyrrolidinone/vinyl acrylate copolymers, vinyl pyrrolidinone, vinyl pyrrolidinone/vinyl acetate copolymers, polyethylene glycols, ethylene/propylene/styrene copolymers and/or butylene/ethylene/styrene copolymers.

Agents (a) and (b) as contemplated herein can also contain further active substances, auxiliaries and additives, for example anionic, zwitterionic, amphoteric and/or cationic surfactants, cationic polymers such as quaternised cellulose ethers, polysiloxanes with quaternary groups, dimethyldiallyl ammonium chloride polymers, acrylamide-dimethyldiallyl ammonium chloride copolymers, dimethylaminoethylmethacrylate-vinyl pyrrolidinone copolymers quaternised with diethyl sulfate, vinyl pyrrolidinone-imidazolinium methochloride copolymers and quaternised polyvinyl alcohol; zwitterionic and amphoteric polymers; anionic polymers such as polyacrylic acids or crosslinked polyacrylic acids; structurants such as glucose, maleic acid and lactic acid, hair-conditioning compounds such as phospholipids, for example lecithin and kephalins; perfume oils, dimethyl isosorbide and cyclodextrins; fibre-structure-improving active substances, in particular mono-, di- and oligosaccharides such as glucose, galactose, fructose, fruit sugar and lactose; dyes for staining the agent; anti-dandruff active substances such as piroctone olamine, zinc omadine and climbazole; amino acids and oligopeptides; protein hydrolysates on an animal and/or vegetable basis, and in the form of their fatty acid condensation products or optionally anionically or cationically modified derivatives; vegetable oils; light stabilisers and UV blockers; active substances such as panthenol, pantothenic acid, pantolactone, allantoin, pyrrolidinone carboxylic acids and their salts and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetration substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments and propellants such as propane-butane mixtures, $N_2O$, dimethyl ether, $CO_2$ and air. In this context, explicit reference is made to the known monographies, e.g. Kh. Schrader, Grundlagen and Rezepturen der Kosmetika [Cosmetic principles and formulas], $2^{nd}$ Edition, Htithig Buch Verlag, Heidelberg 1989, which reflect the corresponding knowledge of a person skilled in the art.

Decolourisation of Dyed Keratin Fibres

The multi-component packaging unit as contemplated herein is a system comprising agents (a) and (b), which is used for the decolourisation of previously dyed keratinous fibres, particularly human hair. The dyed keratin fibres are usually fibres which have been coloured beforehand by employing conventional oxidation dyes and/or substantive dyes known to a person skilled in the art.

The decolourising agents are suitable for removing colours produced on the keratin fibres by employing oxidation dyes based on developer and coupler components. If the following compounds were used as developers, the colours thus produced can easily be removed effectively and almost without subsequent post-darkening by use of the decolourising agent: p-phenylenediamine, p-toluene diamine N,N-bis-β-hydroxy ethyl)-p-phenylenediamine, 4-N,N-bis-(β-hydroxyethyl)-amino-2-methylaniline, 2-(β-hydroxyethyl)-p-phenylenediamine, 2-(α, β-dihydroxyethyl)-p-phenylenediamine, 2-hydroxymethyl-p-phenylenediamine, bis-(2-hydroxy-5-aminophenyl)-methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine and/or 4,5-diamino-1-(β-hydroxyethyl)-pyrazole.

If the following compounds were used as couplers, the colours produced thereby can likewise be removed with very good decolourisation results: m-phenylenediamine derivatives, naphthols, resorcinol and resorcinol derivatives, pyrazolones and m-aminophenol derivatives. Suitable coupler substances are, in particular, 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2',4'-diaminophenoxy) propane, 2-chloro-resorcinol, 4-chloro-resorcinol, 2-chloro-6-methyl-3-aminophenol, 2-amino-3-hydroxypyridine, 2-methylresorcinol, 5-methylresorcinol and 2-methyl-4-chloro-5-aminophenol. 1-naphthol, 1,5-dihydroxynaphthaene, 2,7-dihydroxynaphthalene, 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

The substrate to be decolourised may also have been dyed with substantive dyes. Nitrophenylenediamines, nitroaminophenols, azo dyes, anthraquinones or indophenols are particularly suitable substantive dyes. Preferred substantive dyes are the compounds known under the following international names or trade names: HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 and 1,4-diamino-2-nitrobenzene, 2-amino-4-nitrophenol, 1,4-bis-((3-hydroxyethyl)-amino-2-nitrobenzene, 3-nitro-4-(β-hydroxyethyl)-aminophenol, 2-(2'-hydroxyethyl)amino-4,6-dinitrophenol, 1-(2'-hydroxyethyl)-amino-5-chloro-2-nitrobenzene, 4-amino-3-nitrophenol, 1-(2'-ureidoethyl) amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

Furthermore, the substrates to be decolourised can also be dyed using natural dyes occurring in nature, as are contained for example in henna red, henna neutral, henna black, chamomile blossom, sandalwood, black tea, cascara bark, sage, logwood, madder root, catechu, sedr, and alkanet root.

The decolourising agents as contemplated herein are designed to remove said colours and therefore themselves preferably contain no dyes, i.e. no oxidation dye precursors of the developer type and of the coupler type, as well as no substantive dyes.

In a further preferred embodiment a multi-component packaging unit (kit-of-parts) as contemplated herein is exemplified in that
the total amount of all dyes and oxidation dye precursors contained in agent (a) has a value of at most about 0.2% by weight, preferably at most about 0.1% by weight, more preferably at most about 0.05% by weight and particularly preferably at most about 0.01% by weight—in relation to the total weight of the agent (a)—and
the total amount of all dyes and oxidation dye precursors contained in agent (b) has a value of at most about 0.2% by weight, preferably at most about 0.1% by weight, more preferably at most about 0.05% by weight and particularly preferably at most about 0.01% by weight—in relation to the total weight of the agent (b).

Ready-to-Use Decolourising Agent

The ready-to-use decolourising agent is produced by mixing the two agents (a) and (b) from containers (A) and (B) and is applied to the dyed keratin fibres or hair.

A second subject of the present disclosure is therefore a ready-to-use agent for the reductive decolourisation of dyed keratinous fibres, containing
(a1) one or more reducing agents from the group of formamidine sulfinic acid, sodium dithionite, zinc dithionite, potassium dithionite, hydroxymethane sulfinic acid, aminomethane sulfinic acid, cysteine, thiolactic acid, sulfanyl acetic acid (thioglycolic acid) and/or ascorbic acid, and
(a2) one or more oxidants from the group of sodium percarbonate, potassium percarbonate, sodium perborate, potassium perborate, carbamide peroxide, ammonium persulfate, potassium persulfate and sodium persulfate, and
(b1) one or more alkalising agent(s) from the group 2-aminoethan-1-ol, 2-amino-2-methylpropan-1-ol, ammonia, arginine, lysine, ornithine, histidine, potassium hydroxide, sodium hydroxide, magnesium hydroxide, calcium hydroxide, sodium metasilicate, potassium metasilicate, potassium hydroxide, sodium hydroxide, sodium carbonate, potassium carbonate, sodium hydrogen carbonate and potassium hydrogen carbonate.

In the sense of the present disclosure a ready-to-use decolourising agent is understood to mean an agent which has been mixed just before application—i.e. within a period of at most one hour before application—by mixing the previously described agents (a) and (b) with one another.

By mixing agents (a) and (b), optimal conditions for the reductive decolourisation process are produced, such that the reducing agents contained in the agent react over the course of a few hours, at most a day. In the case of an agent which contains the combination of ingredients (a1), (a2) and (b1) over longer periods of time, the reducing agents are already reacted to such an extent that it is no longer possible to achieve a significant decolourisation result. Such an agent is therefore not a ready-to-use decolourising agent in the sense of the present disclosure.

In a very particularly preferred embodiment the ready-to-use agent as contemplated herein comprises
(a1) formamidine sulfinic acid.

In a very particularly preferred embodiment the ready-to-use agent as contemplated herein contains—in relation to its total weight—one or more reducing agents (a1) in a total amount of from about 2.0 to about 40.0% by weight, preferably from about 3.0 to about 30.0% by weight, more preferably from about 4.0 to about 20.0% by weight, and very particularly preferably from about 5.0 to about 10.0% by weight.

In a very particularly preferred embodiment the ready-to-use agent as contemplated herein comprises
(a2) sodium percarbonate.

In a very particularly preferred embodiment the ready-to-use agent as contemplated herein contains—in relation to its total weight—one or more oxidants (a2) in a total amount of from about 0.1 to about 15.0% by weight, preferably from about 0.4 to about 10.0% by weight, more preferably from about 0.7 to about 8.0% by weight, and very particularly preferably from about 1.1 to about 3.5% by weight.

In a very particularly preferred embodiment the ready-to-use agent as contemplated herein is exemplified in that the ratio by weight of the total amount of all reducing agents (a1) contained in the ready-to-use agent to the total amount of all solid oxidants (a2) contained in the ready-to-use agent, i.e. the ratio by weight (a1)/(a2), lies at a value of from about 50.0 to about 2.0, preferably from about 30.0 to about 3.0, particularly preferably from about 10.0 to about 4.0.

In a very particularly preferred embodiment the ready-to-use agent as contemplated herein contains one or more fat constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils.

In a very particularly preferred embodiment the ready-to-use agent as contemplated herein comprises
(b1) one or more alkalising agents from the group of 2-aminoethan-1-ol, 2-amino-2-methylpropan-1-ol and ammonia.

In a very particularly preferred embodiment the ready-to-use agent as contemplated herein contains water and has a pH value of from about 7.5 to about 12.5, preferably from about 8.0 to about 11.5, more preferably from about 8.5 to about 10.5, and particularly preferably from about 8.5 to about 9.5.

All further very particularly preferred embodiments are those that have already been described for the kit-of-parts as contemplated herein.

Procedure

The above-described multi-component packaging units (kit-of-parts) can be used in processes for reductive decolourisation.

A third subject of the present disclosure is a method for the reductive decolourisation of dyed keratinous fibres, comprising the following steps in the stated order (I) producing a ready-to-use decolourising agent by mixing a first agent (a) with a second agent (b), wherein
   agent (a) is an agent as has been disclosed in detail in the description of the first subject of the present disclosure, and
   agent (b) is an agent as has been disclosed in detail in the description of the first subject of the present disclosure,
(II) applying the ready-to-use decolourising agent to dyed keratinous fibres,
(III) leaving the decolourising agent to take effect
(IV) rinsing out the decolourising agent from the keratinous fibres.

In other words, a third subject of the present disclosure is a method for the reductive decolourisation of dyed keratinous fibres, comprising the following steps in the stated order (I) producing a ready-to-use decolourising agent by mixing a first agent (a) with a second agent (b), wherein
   agent (a) contains
   (a1) one or more reducing agents which are solid at room temperature and which are preferably selected from the group of formamidine sulfinic acid, sodium dithionite, zinc dithionite, potassium dithionite, hydroxymethane sulfinic acid, aminomethane sulfinic acid, cysteine, thiolactic acid, sulfanyl acetic acid (thioglycolic acid) and/or ascorbic acid, and
   (a2) one or more oxidants which are solid at room temperature and which are preferably selected from the group of sodium percarbonate, potassium percarbonate, sodium perborate, potassium perborate, carbamide peroxide, ammonium persulfate, potassium persulfate and sodium persulfate, and
   and
   agent (b) contains
   (b1) one or more alkalising agent(s) which are preferably selected from the group 2-aminoethan-1-ol, 2-amino-2-methylpropan-1-ol, ammonia, arginine, lysine, ornithine, histidine, potassium hydroxide, sodium hydroxide, magnesium hydroxide, calcium hydroxide, sodium metasilicate, potassium metasilicate, potassium hydroxide, sodium hydroxide, sodium carbonate, potassium carbonate, sodium hydrogen carbonate and potassium hydrogen carbonate.
(II) applying the ready-to-use decolourising agent to dyed keratinous fibres,
(III) leaving the decolourising agent to take effect
(IV) rinsing out the decolourising agent from the keratinous fibres.

In step (I) the ready-to-use decolourising agent is produced by mixing agents (a) and (b). The agents (a) and (b) correspond to the two agents of the multi-component packaging unit as contemplated herein. With regard to further preferred embodiments of the agents (a) and (b), that which has been said in relation to the multi-component packaging unit as contemplated herein applies mutatis mutandis.

In step (II) the ready-to-use agent produced by mixing agents (a) and (b) is applied to the keratinous fibres or hair. With regard to further preferred embodiments of the ready-to-use agent, that which has been said in relation to the multi-component packaging unit as contemplated herein applies mutatis mutandis.

Due to the above-described exothermic reaction which is initiated by mixing agents (a) and (b), the ready-to-use agent heats up. This heating ensures complete dissolution of the reducing agents (a1), but on the other hand can also be utilised to further enhance the decolourisation result. The tests performed within the scope of the present disclosure have shown that the application of the heated agent (in comparison to the application of the agent at room temperature) leads to a further improvement of the decolourisation result. In order to utilise this further advantage, it is very particularly preferred if a period of from about 10 seconds to about 30 minutes, preferably from about 10 seconds to about 15 minutes, and very particularly preferably from about 10 seconds to about 10 minutes is provided between steps (I) and (II). In other words it is very particularly preferred if a period of at most about 20 minutes, preferably about 15 minutes, particularly preferably about 10 minutes, is provided between the production of the ready-to-use agent and application thereof to the hair.

In a further embodiment it is very particularly preferred if a period of from about 10 seconds to about 30 minutes, preferably from about 10 seconds to about 15 minutes, and very particularly preferably from about 10 seconds to about 10 minutes is provided between steps (I) and (II).

After application of the ready-to-use decolourising agent to dyed keratinous fibres (step (II)), the ready-to-use decolourising agent is left to take effect on the keratin fibres. The application period may be selected here depending on the desired decolourisation intensity. For example, the decolourising agent may be left to act on the hair for a period of from about 5 to about 60 minutes, preferably from about 10 to about 55 minutes, more preferably from about 20 to about 50 minutes, and particularly preferably from about 30 to about 45 minutes.

In a further embodiment a method is very particularly preferred which is exemplified in that the agents (a) and (b) are mixed with one another in a ratio (a)/(b) of from about 0.1 to about 1.0, preferably from about 0.15 to about 0.9, more preferably from about 0.18 to about 0.8, and very particularly preferably from about 0.2 to about 0.5.

In a further embodiment a method is very particularly preferred which is exemplified in that the mixture of agents (a) and (b) (i.e. the ready-to-use decolourising agents) contains water and has a pH value of from about 7.5 to about 12.5, preferably from about 8.0 to about 11.5, more preferably from about 8.5 to about 10.5, and particularly preferably from about 8.5 to about 9.5.

With regard to further preferred embodiments of the method as contemplated herein, that which has been said in relation to the multi-component packaging unit as contemplated herein and the ready-to-use agent applies mutatis mutandis.

EXAMPLES

1.1. Colouration

The following formulations were produced (all values in % by weight):

| Dye cream (F1) | |
|---|---|
| Raw material | % by weight |
| Cetearyl alcohol | 8.5 |
| C12-C18 fatty alcohols | 3.0 |
| Ceteareth-20 | 0.5 |
| Ceteareth-12 | 0.5 |
| Plantacare 1200 UP (lauryl glucoside, 50-53% aqueous solution) | 2.0 |
| Sodium Laureth-6 Carboxylate (21% aqueous solution) | 10.0 |
| Sodiummyreth Sulfate (68-73% aqueous solution) | 2.8 |
| Sodium acrylate, trimethylammoniopropylacrylamide chloride copolymer (19-21% aqueous solution) | 3.8 |
| Potassium hydroxide | 0.83 |
| p-toluene diamine, sulfate | 0.49 |
| m-aminophenol | 0.023 |
| Resorcinol | 0.17 |
| 2-methylresorcinol | 0.03 |
| 2-amino-3-hydroxypryridine | 0.03 |
| Ammonium sulfate | 0.1 |
| Sodium sulfite | 0.4 |
| Ascorbic acid | 0.1 |
| 1-hydroxyethan-1,1-diphosphonic acid (60% aqueous solution) | 0.2 |
| Ammonia (25% aqueous solution) | 7.2 |
| Water | to 100 |

| Oxidant (Ox) | |
|---|---|
| Raw material | % by weight |
| Sodium benzoate | 0.04 |
| Dipicolinic acid | 0.1 |
| Disodiumpyrophosphate | 0.1 |
| Potassium hydroxide | 0.09 |
| 1,2-propylene glycol | 1.0 |
| 1-hydroxyethan-1,1-diphosphonic acid (60% aqueous solution) | 0.25 |
| Paraffinum Liquidum | 0.30 |
| Steartrimonium chloride | 0.39 |
| Cetearyl alcohol | 3.4 |
| Ceteareth-20 | 1.0 |
| Hydrogen peroxide (50% aqueous solution) | 12.0 |

The dye cream (F1) and the oxidant (Ox) were mixed in the ratio 1:1 and applied to hair strands (Kerling Euro natural hair, white). The ratio of mixture to hair was 4:1, and the reaction time was 30 minutes at a temperature of 32 degrees Celsius. The strands were then rinsed with water, dried and left for at least 24 hours at room temperature. The strands were dyed in a reddish, golden brown shade.

1.2. Decolourisation

The containers (A) and (B) were filled with the following agents (all values in grams):

| Container (A) containing 20 g of agent (a) | | |
|---|---|---|
| Paste | Agent (aV) | Agent (aE) |
| Formamidine sulfinic acid | 8.00 g | 8.00 g |
| Ceteareth-12 | 0.8 g | 0.8 g |
| Ceteareth-20 | 0.15 g | 0.15 g |
| Xanthan | 0.15 g | 0.15 g |
| Lanette N (BASF, Cetearyl alcohol, Sodium cetearyl sulfate) | 1.1 g | 1.1 g |
| Hydrogenated Castor Oil | 0.15 g | 0.15 g |
| Sodium percarbonate | — | 1.6 g |
| Paraffinum Liquidum | to 20.00 g | to 20.00 g |

| Container (B) containing 80 g of agent (b) | | |
|---|---|---|
| Emulsion | Agent (bV) | Agent (bE) |
| Cetearyl alcohol | 4.0 g | 4.0 g |
| Monoethanol amine | — | 2.0 g |
| PEG-40 Hydrogenated Castor Oil | 0.80 g | 0.80 g |
| Sodium laureth sulfate ($C_{12}$-$C_{14}$, 2 EO) | 0.54 g | 0.54 g |
| Water | to 80 g | to 80 g |

In order to produce the ready-to-use decolourising agent, 20 g of agent (a) were mixed in each case with 80 g of agent (b) with stirring at room temperature.

The temperature was measured for each mixture, and the time after which all visible solids had fully dissolved was recorded:

| | Ex. 1 Comparison 20 g agent (aV) + 80 agent (bV) | Ex. 2 Comparison 20 g agent (aE) + 80 agent (bE) |
|---|---|---|
| Temperature after 30 seconds stirring | 20° C. | 28° C. |
| Time until complete dissolution of all visible solids | >10 minutes | 6 minutes |

| | Ex. 3 Comparison 20 g agent (aV) + 80 agent (bE) | Ex. 4 Exemplary Embodiment 20 g agent (aE) + 80 agent (bE) |
|---|---|---|
| Temperature after 30 seconds stirring | 23° C. | 33° C. |
| Time until complete dissolution of all visible solids | 5 minutes | 1 minute |

10 minutes after the mixing of agents (a) and (b), the ready-to-use decolourising agent was applied to the previously dyed hair strands, was left there for 60 minutes at room temperature and was then rinsed out again. The hair strands were then dried.

The colour of the strands decolourised in this way was assessed visually. The colour intensity was assessed on the basis of the following scale:

0—strand no longer has any perceptible colour (white blonde, similar to the original colour of the used Kerling Euro natural hair, white)
1—strand coloured with weak colour intensity
2—strand coloured with medium colour intensity
3—strand coloured with strong colour intensity 4—colour of the strand similar to that directly after the dyeing process, no decolourisation effect

|  | Ex. 1 Comparison | Ex. 2 Comparison | Ex. 3 Comparison | Ex. 4 Exemplary Embodiment |
|---|---|---|---|---|
| Colour of the strands once the decolourising agent has been applied and rinsed out | 3 | 3 | 2 | 1-2 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A ready-to-use agent for reductive decolourisation of dyed hair comprising,
    a cosmetic agent (a) consisting of formamidine sulfinic acid, ceteareth-12, ceteareth-20, xanthan, cetearyl alcohol, sodium cetearyl sulfate, hydrogenated castor oil, sodium percarbonate, and liquid paraffin, and
    a cosmetic agent (b) consisting of cetearyl alcohol, monoethanol amine, PEG-40 hydrogenated castor oil, sodium laureth sulfate, and water.

2. A method for reductive decolourisation of dyed hair, comprising the following steps in the stated order,
    (I) producing a ready-to-use decolourising agent by mixing a cosmetic agent (a) with a cosmetic agent (b), wherein the cosmetic agents (a) and (b) are according to claim 1,
    (II) applying the ready-to-use decolourising agent to the dyed hair,
    (III) leaving the ready-to-use decolourising agent on the dyed hair to take effect, and
    (IV) rinsing out the ready-to-use decolourising agent from the hair.

3. The method according to claim 2, wherein the cosmetic agents (b) and (a) are mixed with one another in a ratio (b)/(a) of from about 10.0 to about 1.0.

* * * * *